United States Patent [19]

Friedmann

[11] 4,346,103
[45] Aug. 24, 1982

[54] TREATMENT FOR ARTHRITIS AND SUBSTANCES FOR USE IN SUCH TREATMENT

[76] Inventor: Charles A. Friedmann, Quattroventi, Montefili, Creve in Chianti, Florence, Italy

[21] Appl. No.: 264,817

[22] Filed: May 18, 1981

Related U.S. Application Data

[63] Continuation of Ser. No. 112,824, Jan. 17, 1980, abandoned, which is a continuation-in-part of Ser. No. 773,406, Mar. 1, 1977, abandoned.

[30] Foreign Application Priority Data

Mar. 16, 1976 [ZA] South Africa ................... 76/1627

[51] Int. Cl.$^3$ ................ A61K 31/12; A61K 31/19; A61K 31/235
[52] U.S. Cl. ............................... 424/308; 424/317; 424/331
[58] Field of Search .................... 424/317, 331, 308

[56] References Cited

U.S. PATENT DOCUMENTS

| | | | |
|---|---|---|---|
| 1,935,928 | 11/1933 | Zahn et al. | 260/351 |
| 2,881,173 | 4/1959 | Wenner | 260/350 |
| 3,873,538 | 3/1975 | Oxford et al. | 260/376 |
| 3,974,186 | 8/1976 | Fleming et al. | 260/376 |

*Primary Examiner*—Stanley J. Friedman
*Attorney, Agent, or Firm*—Cushman, Darby & Cushman

[57] ABSTRACT

The treatment of multiple sclerosis with 1,8-dialkyloxy-3 carboxy anthraquinone.

4 Claims, No Drawings

TREATMENT FOR ARTHRITIS AND SUBSTANCES FOR USE IN SUCH TREATMENT

CROSS-REFERENCE TO RELATED APPLICATIONS

This application is a Continuation of my earlier application Ser. No. 112,824 filed Jan. 17, 1980, and now abandoned, which in turn is a Continuation-In-Part of my earlier application Ser. No. 773,406 filed Mar. 1, 1977, and now abandoned.

This invention relates to the treatment of diseases and in particular arthritis, multiple sclerosis and other diseases in which the myelin covering the nerves is destroyed.

Arthritis, both rheumatoid and osteo, has been treated using anti-inflammatory substances of the corticosterciod type, e.g. hydrocortisone, and betamethozone, which function by virtue of their anti-inflammatory action.

Other compounds used in the treatment of arthritis include anti-inflammatory substances of a non-steroid type such as indomethacin, and ketobrufen and aspirin. These substances function symptomatically and prevent synthesis of prostaglandins, the pain causing agents, which are released by the arthritic process.

More recent approaches to the treatment of arthritis involve the use of substances which have a direct action on specific tissues affected by the arthritic process, that is, particularly on the collagenous networks, on DNA (deoxyribonucleic acid) and on synovial membrane. Amongst such substances are the cytotoxic agents such as cyclophosphamide which acts on DNA, and most recently, the substance penicillamine.

Penicillamine chelates with metals, in particular copper, of which there are increased blood serum levels in arthritis, probably secondary to the presence of increased serum levels of caeruloplasmin (a-2-globulin) in the acute phase of inflammation, and also possibly a co-factor of catalytic oxidases, which would increase the number of disulphide bonds and thus favour production of macroglobulins of the rheumatoid factor type.

Penicillamine depolymerizes rheumatoid factor by opening disulphide bonds which form the cross-linkages that are responsible for the tertiary protein structure of this factor.

From a study of the known therapeutic activities of drugs useful in the treatment of arthritis, I believe that it is likely that an efficient therapeutic agent should have the following properties:

1. It should chelate with copper to stop the formation of caeruloplasmin present in the acute phase of arthritic inflammation.
2. It should inhibit those catalytic oxidases which might increase the number of disulphide bonds with resultant formation of rheumatoid factor.
3. It should be able to chelate with calcium so as to remove the irritant calcium-based microdeposits found in the arthritic joints.
4. It should be able to assist in the formation of cross-linkages in the collagen of synovial membrane which is deficient in these cross-linkages in the case of arthritis.
5. It should be relatively non-toxic and should be able to be taken orally with only very occasional medical supervision.

Penicillamine may need to be taken by injection and can cause very severe side effects. I believe that 1,8-dihydroxyanthra-quinone-3-carboxylic acid, rhein, may approach these desiderata. I believe rhein celates with copper and calcium in the following way

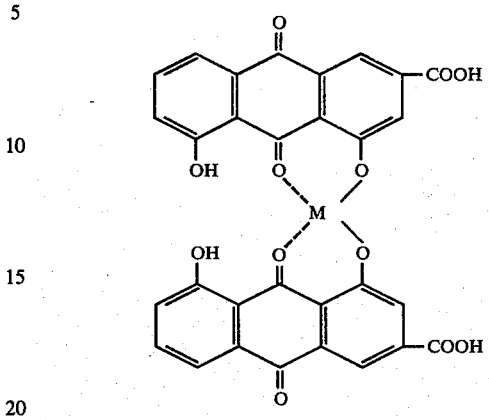

Rhein is an inhibitor of NADH-linked oxidation specifically interfering with the redox function of NADH-dehydrogenase complex and thus with mitochondrial oxidations.

Since quinones are known to form cross-links in tropocollagen, the quinonoid structure of rhein would assist it to function as a corss-linking agent.

Rhein is relatively non-toxic (see below) and functions by oral ingestion. It has been taken for long periods of time, without any apparent side-effects, in the dosage required.

Rhein occurs both in nature, in various plants and also as a metabolic breakdown product when senna glycosides are ingested by humans.

As mentioned above rhein chelates with calcium and with copper. The resulting complex is made water-soluble by the carboxyl group in position 3 of rhein which, in form of its salts, forms a water-soluble chelate.

I believe this solubility is necessary since the space between joints in arthritis contains irritant microcrystalline calcium phosphate, which needs to be dissolved away.

Anthraquinones which do not have such solubilizing groups, e.g. 1,8-dihydroxyanthraquinone, form insoluble chelates with, for example the calcium of bone. These are red coloured compounds that subsequently interfere with bone metabolism.

Accordingly, in one aspect, the present invention provides a method of treating a disease comprising administering an effective amount of a pharmaceutical or veterinary formulation or composition which comprises an antraquinone derivative of the formula:

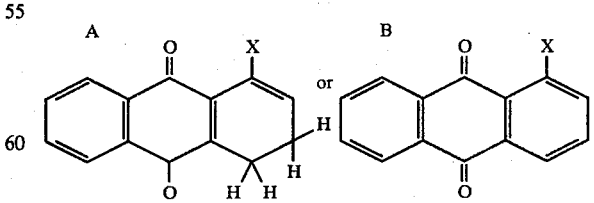

in which formulae X is an —NH$_2$ group, an —OH group or a physiologically hydrolysable ester thereof, in either of which formulae there is a further substituent of at least one solubilising group (as hereinafter defined) and which may be further substituted in the 4,5 or 8 position with not more than one additional hydroxyl group or a physiologically hydrolysable ester thereof, and which may be further substituted with one or more physiologically inactive substituents (as hereinafter defined), providing that when X is an —OH group or a physiologically hydrolysable ester thereof the solubilising group is not a —COOH group in the 2- or 7-position of the molecule, and a pharmaceutically acceptable diluent, carrier or excipient.

It is currently believed that the presence of an —$NH_2$ group attached to an aromatic carbon atom may render the compound concerned carcinogenic. While I do not know for certain whether the anthraquinone derivatives in which —X is —$NH_2$ are carcinogenic, their use should be carefully considered in view of this possibility.

Groups which are pharmacologically equivalent to the phenolic hydroxyl groups in the 1,4,5 or position include esters derived or derivable from such phenolic hydroxyl groups. Esters that may be employed include those of alkanoic acids, preferably having 12 carbon atoms or less, such as acetic and propionic acids, cyclohexanecarboxylic acid, and various phosphoric acids. I believe that these esters will be hydrolysed in the body, under enzymic catalysis, to produce the pharmacologically active hydroxyl derivative.

Preferably, when ingested orally, the anthraquinone derivatives are in the ester form. It has been found in the case of rhein that it adheres strongly to the intestinal mucosa, and should thus be relatively poorly absorbed. If the phenolic hydroxyl groups are protected by esterification, absorption is often more rapid.

By the term "solubilising group" as used herein is meant a group which permits a substantial amount of the anthraquinone derivative to cross the intestinal membrane and enter the bloodstream where it forms water-soluble calcium chelates.

Suitable "solubilising groups" include any group selected from —$(CH_2)_n$—COOH, —CHOH—$(CH_2)_n$—COOH, —CO—$(CH_2)_n$—COOH, —$CH_2$—O—$(CH_2)_n$—COOH, —$CH_2$—O—CO—$(CH_2)_n$—COOH, —O—$(CH_2)_n$—COOH, —$CH_2NH_2$, —$CH_2NHMe$, —$CH_2$—$NMe_2$, —$CH_2NHEt$, —$CH_2$—$NEt_2$, —$SO_3H$ or —$SO_2NH_2$ wherein n is 0, or any integer, preferably 10 or less, and pharmaceutically acceptable salts thereof or pharmacological equivalents thereof.

The solubilising group may be silified. If the solubilising group is acidic, then the salt may be, for example, a sodium, potassium, calcium or ammonium salt. It may be manufactured by treating the acid with the corresponding alkali. However, especially in those cases where the phenolic groups are esterified, those of skill in the art will recognize that considerable care is required to prevent hydrolysis of the phenolic ester in too alkaline a medium. If the solubilising group is an amine, then the salt may be, for example, the hydrochloride or a quarternary ammonium salt.

If the solubilising group is a carboxylic acid, then physiologically hydrolysable esters of this acid may be wed, hydrolysing in the body to the free acid. Preferred esters are the ethyl esters.

While the solubilising group may be in any of the 2-, 3-, 6- or 7-positions it is preferred that the solubilising group should be a substituent in either the 2- or 3-position, most preferably the 3-position. It is often found that it is most convenient to synthesise compounds substituted in these positions.

If there are two solubilising groups, it is preferred that these should be substituents on different rings. One group is then in the 2- or 3-position and the other in the 6- or 7-position. The second solubilising group is most preferably in the 6-position. The two solubilising groups may be the same or different.

The anthraquinone derivatives used in the compositions of the invention may also have one or more physiologically inactive substituents.

By the term "physiologically inactive substituent" as used herein is meant a group which is not essential for conferring anti-osteoarthritic properties on the molecule and which does not increase unwanted side effects.

Preferred "inactive substituents" are methyl, ethyl, propyl, butyl, methoxy or ethoxy groups, or chlorine, bromine or iodine atoms.

The physiologically inactive substituents may be in any otherwise unsubstituted substitutable position, that is in any of the positions 2- to 8-, but not the 9- or 10- positions which have no substitutable hydrogen atoms. There may be more than one physiologically inactive substituent, which may be the same or different. A convenient physiologically inactive substituent is a methoxy group in the 2-position. This compound can be produced from alizarin, 1,2-dihydroxyanthraquinone, and the derivatives of 1-hydroxy-2-methoxyanthraquinone having a solubilising group in the 3 position can often be easily made.

I have further found that this treatment in addition to its efficacy in treating arthritis is effective in the treatment of multiple sclerosis (MS) and amylatropic lateral sclerosis (ALS). It is also useful in the treatment of diseases of other diseases in which procolitic enzymes cause the destruction of the myelin covering of nerves such as encephalomyolitis.

The invention further provides according to another aspect a pharmaceutical or veterinary formulation or composition which comprises an anthraquinone derivative of the formula A or formula B in which formulae X is an —$NH_2$ group, an —OH group or a physiologically hydrolysable ester thereof, in either of which formulae there is a further substituent of at least one solubilising group (as hereinafter defined) and which may be further substituted in the 4,5 or 8 position with not more than one additional hydroxyl group or a physiologically hydrolysable ester thereof, and which may be further substituted with one or more physiologically inactive substituents (as hereinafter defined) providing that when X is an —OH group or a physiologically hydrolysable ester thereof the solubilising group is not a —COOH group in the 2- or 7-position of the molecule.

The solid pharmaceutical composition may be in a pharmaceutical dosage form, which may desirably contain between 10 mg and 300 mg preferably between 25 mg and 100 mg of the anthraquinone derivative. The pharmaceutical dosage form may conveniently be a tablet or pill or a capsule or a suppository.

The pharmaceutical composition may contain fillers or excipients, for example lactose, mannitol, sucrose, calcium sulphate, calcium phosphate and microcrystalline, cellulose, binders, for example tragacanth, acacia, starch and methylcellulose, disintegrants, for example corn starch and alginic acid, or lubricants, for example stearic acid and stearates and talc. Capsules are often of hard gelatin.

The invention may be used to treat both animals of the species homosapiens and other mammals. As a general guide to required daily doses, between about 25 mg and about 500 mg. is convenient for humans, and, at least in adults, is not dependent on body weight of the patient. For animals, as a general guide, between 0.40 mg/kg and 10 mg/kg may be appropriate daily.

It is often not convenient to use the anthraquinone derivatives in aqueous solution, because many of the anthraquinone derivatives may not be sufficiently stable to water. In any individual case, simple tests can be used to ascertain whether there is sufficient stability for any particular purpose.

The invention in a further aspect provides a compound being an anthraquinone derivative derived from formula A or formula B in which formulae X is an —OH or a —NH$_2$ group; in either of which there is a further substituent of at least one, and desirably one or two, solubilising groups, and which may be further substituted with not more than one additional hydroxyl group, or a pharmacological equivalent of a hydroxyl group, which must be in the 4, 5 or 8 positions only, and in which there may be one or more inactive substituents, or the pharmacological equivalent of any such anthraquinone derivative but excluding rhein, and 1-hydroxy-2-(N,N-dimethylaminomethyl-anthraquinone. Rhein is known but has not been proposed for use for the treatment of arthritis. I believe the other disclaimed compound is also known but, if so, has not been proposed for use for the treatment of arthritis.

In an acute toxicity trial, 1,8-diacetoxy-3-carboxyanthraquinone (diacetylrhein) was administered to 26 mice in doses of up to about 3000 mg per kg per day. None of the mice died, nor were any changes noted in behaviour patterns, or in food and water intake; no toxic effects were noted.

No untoward effects were noted during human ingestion of about 100 mg per day of diacetylrhein for 15 months. A human patient having severe osteoarthritis (established by X-ray, CSF and rheumatoid factor assessments) across the lower back was treated with diacetylrhein. The patient had greatly restricted torsal rotation and a notable pain in his back and legs after remaining seated for 30 to 60 minutes. The patient was treated by ingesting two daily doses of 50 mg of diacetylrhein. An effect was noted on the fourth and fifth days and the patient became pain free with restored torsal rotation and without early morning stiffness. With continued treatment the patient maintained his improved condition.

Similar results were achieved with other patients suffering from osteoarthritis of the hips and thighs and of the neck and shoulders.

In three cases, patients with rheumatoid arthritis of the hands, having swollen fingers and painful joints, were treated with 50 mg of diacetylrhein, twice daily for between five and ten days. In each case, the pain in the joints disappeared and was absent even when these were submitted to pressure. The fingers rapidly returned to normal thickness.

I believe that diacetylrhein treats the arthritis in that it stops the progress of arthritis by blocking the release of those enzymes from chondrocytic lysosomes which cause break down of cartilage.

Clinical tests have been carried out on arthritis patients with extremely encouraging results. There has almost never been a failure to respond to this treatment in such tests. Indeed treatment of patients suffering from arthritis of the hip which would otherwise have required submission to the Charnley Hip Operation have made sufficient progress for this to be unnecessary.

Four human patients suffering from MS were treated with diacetylrhein. They were treated by ingesting two daily doses of 50 mg diacetylrhein. The pain and a large part of the limb unsteadiness disappeared within seven to ten days of initiating treatment.

A human patient suffering from ALS in a fairly advanced stage was treated with diacetylrhein over a period of six months. The diacetylrhein was ingested in daily doses increasing up to 150 mg daily.

Deterioration of the patient's condition both as to unsteadiness of gait and weakness of voice was substantially inhibited. The patient's condition was substantially stabilised.

Clinical trials are being carried out in which patients suffering from MS and ALS are being treated with diacetylrhein. The results of such trials have been most encouraging.

In all clinical trials carried out to date with diacetylrhein side effects have been unsignificant. The only side effect I have so far encountered is some diarrhoea which can be eliminated by reducing the dosage.

The following are non-limitative examples of the manufacture of the anthraquinone derivatives.

EXAMPLE 1

Sennosides A and B (10 gms) obtainable, for example by the methods referred to in the Merck Index 8th edition from extracts of senna leaf or pod, are dissolved in 200 mls. of 70% aqueous ethanol containing 5% by volume of concentrated hydrochloric acid and the solution boiled under reflux for 20 minutes. Ferric chloride (200 gms) and glacial acetic acid (200 ml) are then added and the mixture refluxed for a further 3 hours. The ethanol is removed under reduced pressure and the resulting precipitate of crude rhein is collected and recrystallized from glacial acetic acid or dimethylformamide.

EXAMPLE 2

1-amino-4-hydroxyanthraquinone is reacted with a formaldehyde solution and dimethylamine hydrochloride in the presence of sodium dithionite below pH=11. The product, 1-amino-4-hydroxy-2(N:N-dimethylaminomethyl)anthraquinone is reacted with nitrous acid producing 1,4-dihydroxy-2(N:N-dimethylaminomethyl)anthraquinone.

EXAMPLE 3

1-hydroxyanthraquinone-2-oxyacetic acid (solubilizing group is —O—CH$_2$—COOH) is snythesised from alizarin by the method described in Centralblatt 1905,1,703.

EXAMPLE 4

1-hydroxy-2-methoxyanthraquinone-3-sulphonamide is prepared from alizarin by the method described in Beilstein, Volume 6, Page 444.

EXAMPLE 5

1-aminoanthraquinone is reacted with formaldehyde, dimethylamine hydrochloride and sodium dithionite at pH less than 11 to give 1-amino-2(N:N-dimethylaminomethyl)—anthraquinone.

TABLE 1

| Column 1 | Column 2 |
| --- | --- |
| Rhein | 1,8-dihydroxy-3-carboxy-3,4-dihydroanthraquinone |
| 1,4-dihydroxy-2(N;N-dimethylaminomethyl) anthraquinone | 1,4-dihydroxy-2(N,N-dimethylaminomethyl)-3,4-dihydroanthraquinone |
| 1-hydroxyanthraquinone-2-oxyacetic acid | 1-hydroxy-3,4-dihydroanthraquinone-2-oxyacetic acid |
| 1-hydroxy-2(N,N-dimethylaminomethyl) anthraquinone | 1-hydroxy-2(N,N-dimethylaminomethyl)-3,4-dihydro anthraquinone |
| 1,8-dihydroxy-2(N,N-dimethylaminomethyl) anthraquinone | 1,8-dihydroxy-2(N,N-dimethylaminomethyl)-3,4-dihydro anthraquinone |
| 1,8-dihydroxyanthraquinone | 1,8-dihydroxy-3,4-dihydro anthraquinone |

This is treated with nitrous acid to give 1-hydroxy-2(N:N-dimethylaminomethyl)-anthraquinone.

EXAMPLE 6

1-amino-8-hydroxyanthraquinone is treated with formaldehyde, dimethylamine and sodium dithiomite at pH less than 11 to give 1-amino-2(N:N-dimethylaminomethyl)-8-hydroxyanthraquinone. This is reacted with nitrous acid to give 1:8-dihydroxy-2(N:N-dimethylaminomethyl)anthraquinone.

EXAMPLE 7

1,8-diacetoxy-3(hydroxy-methyl)anthraquinone is oxidised with air in refluxing dimethyl sulphoxide to the corresponding 3-aldehyde. The 3-aldehyde is reacted with acidified sodium cyanide to produce its cyanhydrin. The cyanhydrin is hydrolysed with sodium hydroxide to produce 1,8-dihydroxy-3(carboxyhydroxymethyl)anthraquinone.

EXAMPLE 8

The substances in column 1 of Table 1 are treated at room temperature, with hydrogen at between one and two atmospheres pressure, in the presence of Raney nickel catalyst. The products are given in column 2.

EXAMPLE 9

1:8-dihydroxy-3,4-dihydroanthraquinone is reacted with sodium ethoxide and the ethyl ester of 3-bromopropionic acid to give the ethylester of 1,8-dihydroxy-3:4-dihydro-2(2-carboxyethyl)anthraquinone. Gentle hydrolysis at room temperature with dilute sodium hydroxide solution gives the free acid.

EXAMPLE 10

1:8-dihydroxy-3:4-dihydroanthraquinone is reacted with sodium ethoxide and the ethyl ester of bromacetic acid to produce 1:8-dihydroxy-2-(carboxymethyl)-3,4-dihydroanthraquinone.

EXAMPLE 11

1-hydroxy-2(carboxymethyl)-3,4-dihydroanthraquinone is made analogously from 1-hydroxy-3,4-dihydroanthraquinone.

EXAMPLE 12

1-hydroxy-3,4-dihydroanthraquinone is reacted with 2 moles of acetic anhydride in pyridine for 15 hours. The mixture is poured into water, when 1-acetyl-3,4-dihydro-anthraquinone separates. It is collected, washed and dried at 80° C. and 2 Pa absolute (15 torr). The 1-acetyl-3,4-dihydroanthraquinone is reacted with 2 moles of N-bromosuccinimide while suspended in boiling carbon tetrachloride under reflux for 2 hours. 1-acetyl-3-bromo-3,4-dihydroanthraquinone is collected, dissolved in acetone and treated with ethyl 2-bromoacetate and excess copper powder, under reflux, for 2 hours. The ethyl ester of 1-acetoxy-3(carboxymethyl)-3,4-dihydroanthraquinone is collected and hydrolysed by standing overnight in N sodium hydroxide solution under nitrogen. The free acid, 1-hydroxy-3(carboxymethyl)-3,4-dihydroanthraquinone is then obtained on acidification.

EXAMPLE 13

The substances set out in column 1 of Table 2, are dissolved in excess acetic anhydride. A few milliliters of concentrated sulphuric acid are added and the mixture is stood at ambient temperature overnight. The mixture is poured into cold water and the precipitate of the compound set out in the column 2 of the table is obtained.

TABLE 2

| Column 1 | Column 2 |
| --- | --- |
| Rhein | 1,8-diacetoxy-3-carboxyanthraquinone |
| 1,4-dihydroxy-2(N:N-dimethylaminomethylanthraquinone | 1,4-diacetoxy-2(N:N-dimethylaminomethyl)-anthraquinone |
| 1-hydroxyanthraquinone-2-oxyacetic acid | 1-acetoxyanthraquinone-2-oxyacetic acid |
| 1-hydroxy-2-methoxyanthraquinone-3-sulphonamide | 1-acetoxy-2-methoxyanthraquinone-3-sulphon-amide |
| 1,8-dihydroxy-2(N:N-dimethylaminomethyl)anthraquinone | 1,8-diacetoxy-2(N;N-dimethylaminomethyl)-anthraquinone |
| 1-hydroxy-2(2-carboxyethyl)-3,4-dihydroanthraquinone | 1-acetoxy-2(2-carboxyethyl)-3,4-dihydro-anthraquinone |
| 1,8dihydroxy-3(carboxyhydroxymethyl)anthraquinone | 1,8-diacetoxy-3(carboxyhydroxymethyl) anthraquinone |
| 1-hydroxy-2(2-carboxyethyl)-3,4-dihydroanthraquinone | 1-acetoxy-2(2-carboxyethyl)-3,4-dihydroanthraquinone. |
| 1-hydroxy-2(carboxymethyl)-3,4-dihydroanthraquinone | 1-acetoxy-2(carboxymethyl)-3,4-dihydroanthraquinone |

I claim:

1. A method of treating the symptoms of multiple sclerosis comprising administering to a person suffering therefrom an effective amount of 1,8 dialkyloxy-3-carboxy-anthraquinone or a pharmaceutically acceptable ester thereof, in which the alkyl radical is derived from an aliphatic acid having from 1 to 6 carbon atoms.

2. The method of treating the symptoms of multiple sclerosis according to claim 1 in which the compound is 1,8 diacetoxy-3-carboxy-anthraquinone.

3. A method of treating the symptoms of multiple sclerosis according to claim 1 in which said compound is 1,8 dipropyoniloxy-3-carboxy-anthraquinone.

4. The method according to claim 1 wherein between about 25 mg and about 500 mg of the anthraquinone is administered daily to a human.

* * * * *